United States Patent
Dugas et al.

(10) Patent No.: US 7,875,847 B2
(45) Date of Patent: Jan. 25, 2011

(54) DOCKING STAND FOR ANALYTICAL INSTRUMENT

(75) Inventors: Michael E. Dugas, Londonderry, NH (US); Mark Hamilton, Upton, MA (US); Kenneth P. Martin, Watertown, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 217 days.

(21) Appl. No.: 12/200,847

(22) Filed: Aug. 28, 2008

(65) Prior Publication Data
US 2009/0057582 A1    Mar. 5, 2009

Related U.S. Application Data

(60) Provisional application No. 60/968,538, filed on Aug. 28, 2007.

(51) Int. Cl.
*G01J 3/00* (2006.01)
*G01N 21/00* (2006.01)
*B01D 59/44* (2006.01)

(52) U.S. Cl. ............... 250/282; 250/281; 250/284; 250/288

(58) Field of Classification Search ........... None
See application file for complete search history.

(56) References Cited

U.S. PATENT DOCUMENTS

| | | | |
|---|---|---|---|
| 5,521,371 | A | 5/1996 | Hotta et al. |
| 5,705,818 | A | 1/1998 | Kelbel et al. |
| 6,412,642 | B2 | 7/2002 | Charles et al. |
| 6,442,639 | B1 | 8/2002 | McElhattan et al. |
| 6,459,767 | B1 | 10/2002 | Boyer |
| 7,198,174 | B2 | 4/2007 | Sloan |
| 2004/0247080 | A1 | 12/2004 | Feda |
| 2005/0009122 | A1 | 1/2005 | Whelan et al. |
| 2005/0019943 | A1 | 1/2005 | Chaoui et al. |

(Continued)

FOREIGN PATENT DOCUMENTS

CA    2 271 084 A1    5/1998

(Continued)

OTHER PUBLICATIONS

Stan Piorek, "Screening Materials for RoHS Compliance with the Niton XLt Analyzer—The Portable XRF Solution for Electronics Industry," White Paper, XP002519183, (2005).

(Continued)

*Primary Examiner*—David A Vanore
(74) *Attorney, Agent, or Firm*—Sunstein Kann Murphy & Timbers; Charles B. Katz

(57) ABSTRACT

An analytical instrument may be docked in a stand. The stand provides electrical power, cooling, gas to purge air from an analytical gap within the instrument and/or other supplies or services to the instrument. The stand contains a contactless memory, such as an RF-ID tag, which stores information about the supplies and/or services the stand is capable of providing to the instrument. The instrument reads the stand's contactless memory and automatically sets operational parameters of the instrument in accordance with the supplies and/or services the stand is capable of providing. Thus, the instrument may automatically operate in an enhanced mode, such as at a higher x-ray beam power, as a result of being mounted in the stand.

18 Claims, 11 Drawing Sheets

U.S. PATENT DOCUMENTS

| | | | |
|---|---|---|---|
| 2005/0103840 | A1 | 5/2005 | Boles |
| 2007/0140424 | A1 | 6/2007 | Serceki |
| 2007/0174152 | A1 | 7/2007 | Bjornberg et al. |
| 2008/0192897 | A1* | 8/2008 | Piorek et al. ............... 378/98.8 |
| 2009/0064276 | A1* | 3/2009 | Dugas et al. .................... 726/2 |
| 2009/0262889 | A1* | 10/2009 | Dugas et al. .................. 378/45 |
| 2010/0080351 | A1* | 4/2010 | Hession-Kunz et al. ....... 378/45 |
| 2010/0134794 | A1* | 6/2010 | Odegard et al. ............. 356/301 |

FOREIGN PATENT DOCUMENTS

| | | |
|---|---|---|
| EP | 1 191 328 A2 | 3/2002 |
| EP | 1 607 723 A1 | 12/2005 |
| EP | 1 936 539 A1 | 6/2008 |
| WO | WO 2004/027404 A1 | 4/2004 |
| WO | WO 2004/043831 A2 | 5/2004 |
| WO | WO 2007/075922 A2 | 7/2007 |

OTHER PUBLICATIONS

Gregory Farnum, "Will RFID Put the 'Auto' into Auto ID?, " Managing Automation, pp. 51-52, (1994).

Departmrnt of Defense, "Defense Federal Acquisition Regulation Supplement; Radio Frequency Identification," Federal Register, vol. 70 (No. 76), p. 20726-20729, (2005).

Department of Defense, "Defense Federal Acquisition Regulation Supplement; Radio Frequency Identification; Correction," Federal Register, vol. 70 (No. 80), p. 21729, (2005).

Scott J. Horne, "Comments of The Institute of Scrap Recycling Industries, Inc. On Proposed Amendments to the Defense Federal Acquisition Regulations Supplement to Add Policy Pertaining to Package Marking with Passive Radio Frequency Identification Tags," The Institute of Scrap Recycling Industries, Inc. pp. 1-6, (2005).

Donna Pellerin George, "Leaving Las Vegas," Sensors Magazine, pp. 1-4, (2004).

Texas Instruments, "Multi Standard Fully Integrated 13.56-MHz Radio Frequency Identification (RFID) Analog Front End and Data Framing Reader System," TRF7960/61 Product Data Sheet, pp. 1-8, (2006).

Phillip F. Schewe, "All-Optical Magnetic Recording," The American Institute of Physics Bulletin of Physics News, No. 830, (2007).

Weber Marking Systems, Inc., "Alpha RFID Smart Label Applicator," Encoder Verifier web page, http://www.webermarking.com, (2007).

Weber Marking Systems, Inc., "RFID Printing & Encoding Solutions from Weber," RFID Printers/Encoders web page, http://www.webermarking.com, (2007).

Thermo Scientific Niton, "XRF Rentals," Niton XRF Analyzers Product Literature, http://www.niton.com/Rentals-and-Leasing/rentals.aspx, (2007).

* cited by examiner

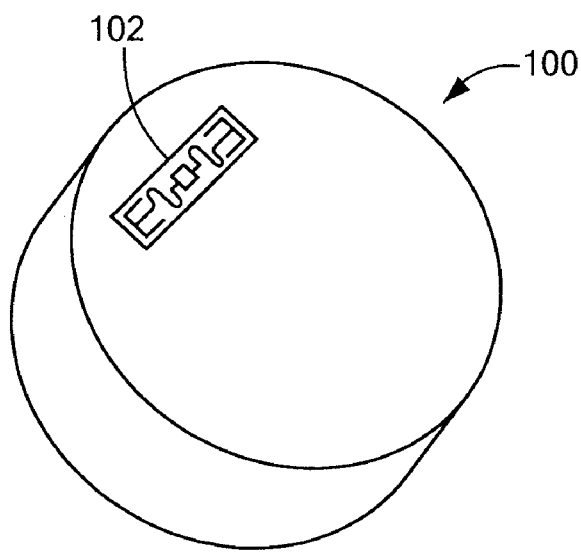
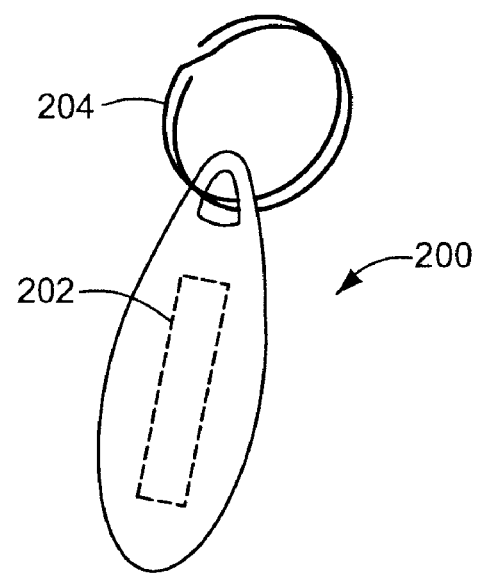
FIG. 1
FIG. 2
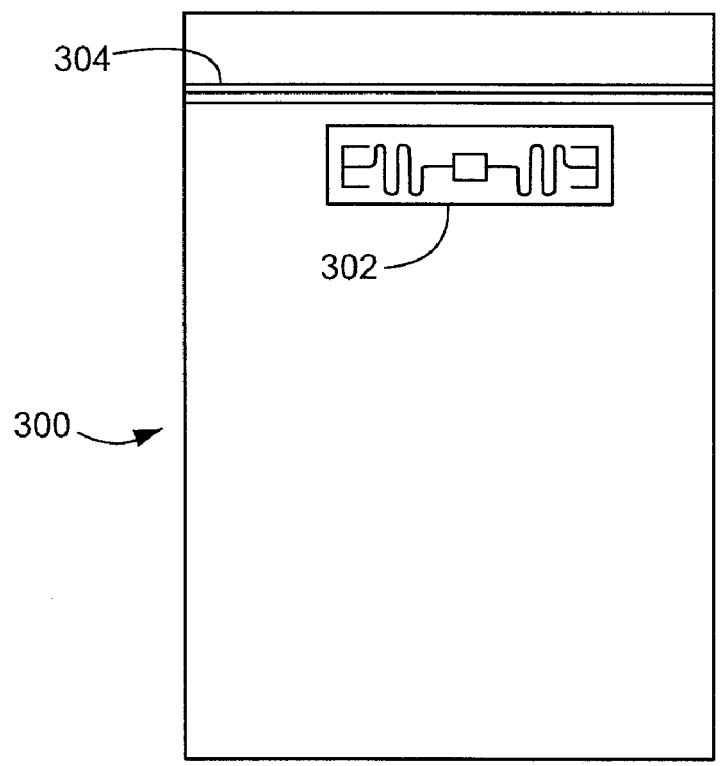
FIG. 3

DOCKING STAND FOR ANALYTICAL INSTRUMENT

CROSS REFERENCE TO RELATED APPLICATIONS

This application claims the benefit of U.S. Provisional Patent Application No. 60/968,538, filed Aug. 28, 2007, titled "Contactless Memory Information Storage for Sample Analysis," the entire contents of which are hereby incorporated by reference herein, for all purposes.

TECHNICAL FIELD

The present invention is also related to automatically setting operating parameters of an analytical instrument, based on capabilities of a stand, in which the instrument is docked.

BACKGROUND ART

Portable and bench-top x-ray fluorescent (XRF), optical emission spectrographic (OES) and other analytical instruments are used throughout the world for determining elemental and chemical compositions of samples, such as metals, soils and plastics. In some cases, results of these analyses are stored in the instruments or archived in company databases, etc., sometimes with user-entered identifying information, such as time and date of analysis, instrument operator's name, etc.

In one common application, such instruments are used in metal recycling facilities to facilitate sorting large and small pieces of scrap metal. In such facilities, the scrap pieces are physically sorted and segregated into piles of similarly composed materials. For example, ferrous metals may be separated from nonferrous metals. After each piece of metal is analyzed, such as with a hand-held instrument, the piece is moved to an area of the recycling facility where similarly composed pieces are stockpiled.

Later, if it becomes desirable to more finely sort the pieces in one stockpile, for example, if it becomes desirable to sort the ferrous metals according to alloy type, each piece in the ferrous stockpile must be analyzed again, and the re-analyzed pieces must be physically moved again to create separate stockpiles of, for example, cast iron, stainless steel, wrought iron, etc. Re-analyzing the pieces and then moving the pieces to the separate stockpiles takes time. Even if the pieces were originally segregated according to alloy, requiring a separate stockpile for each material composition requires a large amount of real estate, because each stockpile must be separated from the other stockpiles by enough space to operate material moving equipment.

In other common applications, such instruments are used to analyze, identify or certify elemental concentrations or chemical compositions of materials. For example, such instruments are used to: quantify the amount of gold or other precious metals in jewelry; identify plastics that have excessive amounts of toxic elements; or certify soil that has less than a predetermined amount of a toxic chemical. However, securely conveying certifications or other information about analyzed materials when the materials change hands is difficult, particularly if the materials are conveyed through a long chain of ownership.

SUMMARY OF THE INVENTION

An embodiment of the present invention provides a method for automatically setting an operating parameter of an analytical instrument. The method includes automatically determining if the analytical instrument is mounted on a stand. If the analytical instrument is determined to be mounted on the stand, the method includes operating the analytical instrument according to a first operating parameter. However, if the analytical instrument is determined not to be mounted on the stand, the method includes operating the analyzer according to a second operating parameter different than the first operating parameter.

Determining if the analytical instrument is mounted on the stand may include determining if the analytical instrument is mounted on a stand that is capable of cooling at least a portion of the analytical instrument and/or providing electrical power to the analytical instrument.

According to the first operating parameter, the analytical instrument may be operated at a higher power rating than according to the second operating parameter.

Optionally or alternatively, determining if the analytical instrument is mounted on the stand may include scanning for a contactless memory associated with the stand. Scanning for the contactless memory may include scanning for a radio-frequency identification (RF-ID) tag, scanning for a barcode and/or reading a magnetic stripe.

Yet an embodiment of the present invention provides a method for automatically preventing unsafe operation of an analytical instrument that can operate in at least two different modes. The method includes automatically determining if the analytical instrument is mounted on a stand. If the analytical instrument is determined to be mounted on the stand, the method may include operating the analyzer according to a first of the at least two different modes only if a safety device on the stand has been activated. However, if the analytical instrument is determined not to be mounted on the stand, the method may include operating the analytical instrument according to a second of the at least two different modes, without determining if the safety device has been activated.

Operating the analytical instrument according to the first mode may include operating a source for producing a beam of penetrating radiation at a first power level and operating the analytical instrument according to the second mode may include operating the source for producing a beam of penetrating radiation at a second power level. The second power level may be less than the first power level.

The safety device may include a closeable cover.

The source for producing a beam of penetrating radiation may include an x-ray tube, a laser and/or a spark source.

Determining if the analytical instrument is mounted on the stand may include scanning for a contactless memory associated with the stand. Scanning for the contactless memory may include scanning for a radio-frequency identification (RF-ID) tag, scanning a barcode and/or reading a magnetic stripe.

An embodiment of the present invention provides a stand for an analytical instrument. The stand includes a receiver for detachably docking an analytical instrument that produces a beam of penetrating radiation. The stand also includes a shield that is substantially opaque to the radiation produced by the analytical instrument. The stand also includes an interlock that prevents production of the radiation by the analytical instrument when the shield is in a first position and allows production of the radiation when the shield is in a second position.

Another embodiment of the present invention provides a system for analyzing composition of a sample. The system includes a stand comprising a recloseable, radiation-shielded enclosure and a hand-held analyzer. The hand-held analyzer is releasably attachable to the stand. The hand-held analyzer includes a source for producing an excitation signal that produces a response signal from the sample. The analyzer is operable in a first mode, in which the source operates at a first power level. The analyzer is also operable in a second mode, in which the source operates at a second power level. The second power level is greater than the first power level. The system also includes an interlock that enables the analyzer to operate in the second mode only if the analyzer is attached to the stand and the enclosure is closed.

The interlock may include a contactless memory attached to the stand and a contactless memory reader in the analyzer. The system may also include a sensor that detects a state of the enclosure.

BRIEF DESCRIPTION OF THE DRAWINGS

The invention will be more fully understood by referring to the following Detailed Description of Specific Embodiments in conjunction with the attached Drawings, of which:

FIG. 1 is a perspective view of an exemplary sample with a radio-frequency identification (RF-ID) tag attached thereto, according to one embodiment of the present invention;

FIG. 2 is a perspective view of a fob that includes an RF-ID tag, according to one embodiment of the present invention;

FIG. 3 is a plan view of a bag, with an RF-ID tag attached thereto, that may be used for loose and other types of samples, according to one embodiment of the present invention;

DETAILED DESCRIPTION OF SPECIFIC EMBODIMENTS

Description

Figure 4:
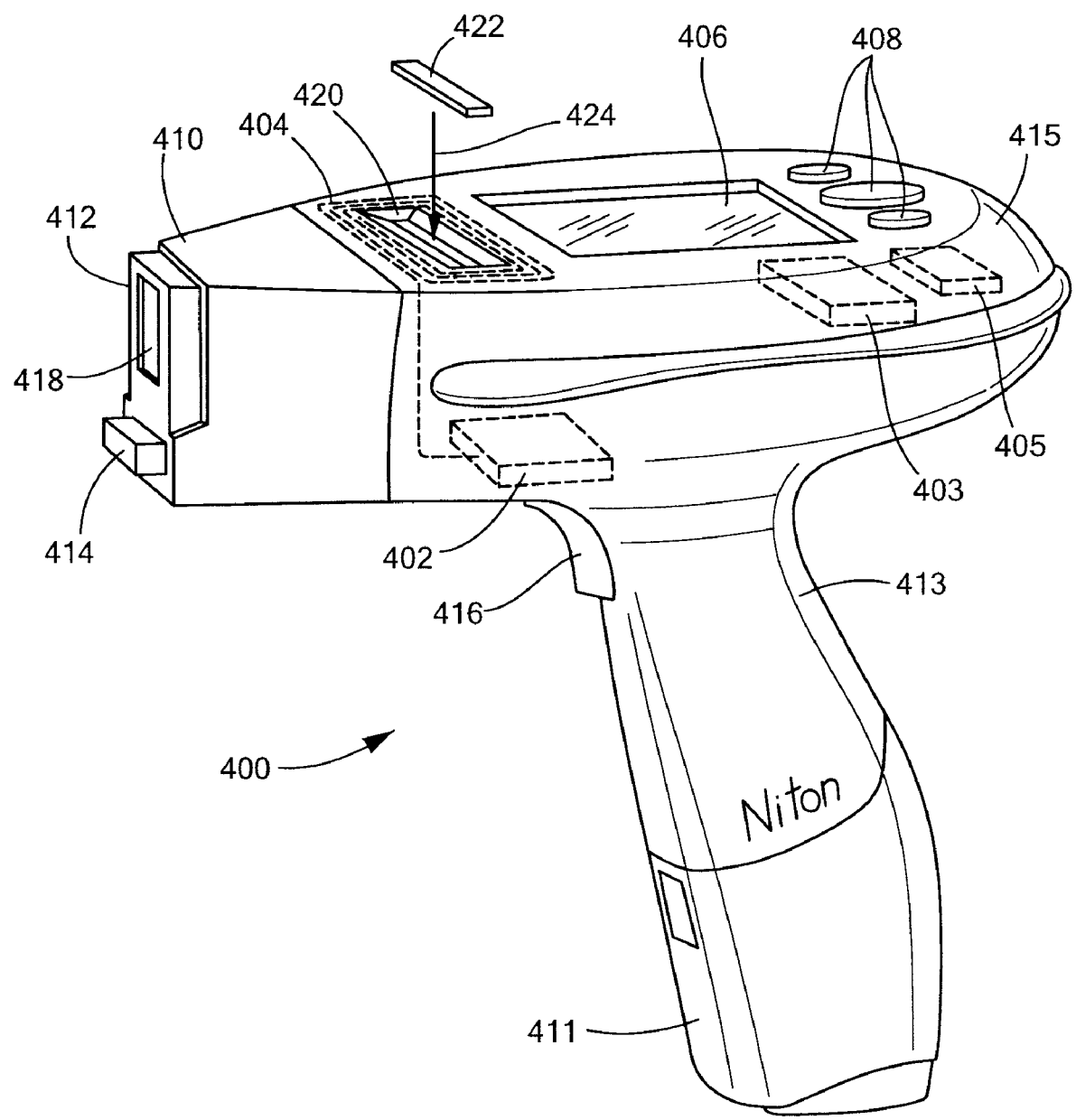
FIG. 4 is a perspective view of an x-ray fluorescence (XRF) instrument that includes an RF-ID reader, writer or reader/writer, according to one embodiment of the present invention.

The contents of U.S. Provisional Patent Application Nos. 60/891,408, titled "Hand-Held, Self-Contained Optical Emission Spectroscopy (OES) Analyzer," filed Feb. 23, 2007, and 60/889,465, titled "Small Spot X-Ray Fluorescence (XRF) Analyzer," filed Feb. 12, 2007, are hereby incorporated by reference herein.

Storing Analytical Information in Association with an Analyzed Sample

In accordance with embodiments of the present invention, methods and apparatus are disclosed for storing information related to an analyzed substance (also referred to as a "sample" or, equivalently, as an "analyte"), such as a metal, soil, a plastic or a composite. The information may be stored in a contactless memory. The term "contactless memory," as used herein, means that the memory, be it read-only or read/write, may be read without electrical contact with the memory and in some embodiments may be written without contact. Exemplary contactless memories include, without limitation: passive or active radio-frequency identification (RF-ID) tags, printed or rewriteable barcodes and magnetic stripes. Although these exemplary contactless memories are discussed and may be used on various embodiments, not all contactless memories are equivalent or necessarily interchangeable. Some contactless memories may be written, whereas other contactless memories are read-only devices. The amount of data that may be stored in a contactless memory may vary with the technology used.

The information about the analyzed sample may include information about: composition of the sample, one or more analytical instruments that were used to analyze the sample, operator(s) who used the instrument(s) to analyze the sample, user-entered data about the sample (such as an origin of the sample) or a combination thereof or the like. The information may be stored in the memory when the sample is analyzed. Optionally, additional information may be added to the memory if the sample is subsequently analyzed again, such as by a second instrument that is sensitive to a different set of constituents or that uses a different analytical protocol. The memory may be attached to the sample or to a container, such as a plastic bag, a box or a rail car, in which the sample is stored or transported. Optionally or alternatively, one or more copies of such a memory may be loosely stored with the sample, such as with soil in a plastic bag or in a rail car.

The memory(ies) may be added to the sample at about the same time that the sample is analyzed and for the purpose of storing the above-described information. However, a memory with sufficient storage capacity may be used to also store other information, such as information about a chain of custody of the sample. Alternatively, a memory that is already associated with the sample may be used for storing the information about the sample's composition, etc. For example, such a memory may have been included with the sample by a manufacturer or another entity in the sample's supply chain for inventory control or another purpose. Thus, the composition information may be able to "piggyback" on, or replace data in, an existing memory. If the manufacturer or other entity in the sample's supply chain stored information about the composition of the sample at the time the sample was manufactured or subsequently, the analytical instrument may verify or refute this compositional information. For example, the sample may have undergone a chemical change since its manufacture due to time, exposure to radiation, contamination or for some other reason.

A sample may be any size. For example, a sample may be small, such as on the order of several centimeters or less in diameter. A sample may be a representative piece cut or otherwise separated from a larger item or volume of material.

On the other hand, a sample may be large. The term "sample" also encompasses an entire item, only a portion of which is analyzed, without cutting or separating the analyzed portion from the rest of the item. For example, a piece of scrap metal in a metal recycling facility may be many meters long, but only one or several portions of the scrap metal may be analyzed.

In some cases, only one portion of a sample is analyzed. In other cases, more than one portion of a sample is analyzed, such as to ascertain uniformity of composition of the sample. Information about several (possibly physically spaced-apart) measurements taken on a single sample may be stored individually, or information representing an average or a composite of several individual measurements may be stored in the memory.

When the memory is attached to, or stored with, the sample, the sample becomes essentially self-documenting. Information about the sample, such as its composition or origin, may be read by a contactless memory reader, such as an RF-ID reader. Thus, many different types of tagged samples may be stockpiled or shipped together. The samples may subsequently be sorted or segregated by reading the information stored in the samples' memories, without re-analyzing the compositions of the samples. Thus, for example, a recycling facility need not separately stockpile each type of material. Instead, after each item has been analyzed and tagged with a memory, a portable hand-held RF-ID reader may be used to manually sort the samples, or an automatic sorter may use an RF-ID reader. In the latter case, the RF-ID reader may be attached to an automatic sorter, such as a conveyor belt-driven sorter. As each sample passes near the RF-ID reader, the automatic sorter may interrogate the memory traveling with, and therefore associated with, the sample and divert the sample to a selected one of several destinations, based on information read from the memory.

Samples' information travels with the samples. An unsegregated mixture of sample types may be transported together and later sorted and re-sorted as needed, based on the information in their respective memories. For example, samples may be sorted according to iron content for one purpose. Some high iron content samples may be removed, and the remaining samples may be mixed back together, moved if necessary, and then sorted again, this time according to sulfur content or state of origin or some other criterion. Thus, the samples need not be physically segregated after their initial analyses. Furthermore, at the time of the initial analyses, no determination needs to be made regarding on what basis the samples should be segregated; that determination may be made and remade later.

Using the disclosed systems and methods, the samples' information is much less likely to be lost than if the information were stored in a paper-based or computerized system, because each sample's information remains physically proximate the sample. Once the sample is analyzed, information about the sample may be obtained quickly and at a location of the sample, without resorting to a central paper file or computer system; the sample's information may be retrieved quickly by simply reading the memory with a portable or non-portable RF-ID reader. Furthermore, when possession of a sample is transferred from one organization to another organization, this information is automatically transferred to the other organization, along with the sample. No paper or electronic data transfer is necessary.

The information in the memory may be encrypted to prevent unauthorized reading of the information. Furthermore, encrypting the information, or storing a digital signature, in the memory may provide a subsequent user of the information with a level of confidence in the accuracy of the information, because the user may ascertain the identity of the person, organization and/or instrument who or that analyzed the sample. Knowledge of this/these identity(ies) enables a user to evaluate the reliability of the compositional or other information in the memory. If an analyzing organization or person is certified to perform a particular type of analysis, and the analytical information in the memory is signed with a digital signature associated with the organization's or person's certificate, a subsequent user of the information may be confident that the analysis was performed by a certified organization or person. In addition, each person or organization who or that handles a sample may add his/her/its identity (such as in the form of a digital signature) to the memory, thus providing a secure chain of custody to the sample.

In addition to storing information about the composition of the sample, the instrument may store additional or other information in the contactless memory, including, without limitation: the type of instrument(s) (e.g., XRF, OES, Raman spectrometer, mass spectrometer, etc.) used to analyze the sample; a range or list of elements, alloys, etc. each analyzing instrument is capable of detecting; minimum quantities or concentrations of the elements, alloys, etc., each analyzing instrument is capable of detecting; a spectral range or list of wavelengths or minimum signal levels each analyzing instrument is capable to detecting; a serial number of each analyzing instrument; or number and location(s) of portions of the sample that were analyzed.

Preventing Unauthorized Use of an Analytical Instrument

In accordance with embodiments of the present invention, methods and apparatus are disclosed for preventing unauthorized persons from operating analytical instruments, such as XRF and OES instruments. Use of some of these instruments by unqualified persons can be dangerous. For example, a typical XRF analyzer produces a potentially dangerous x-ray beam, and a common type of OES instrument produces a high-voltage discharge.

An analytical instrument may include a contactless memory reader, such as an RF-ID reader. Each person authorized to use the instrument may carry a contactless memory, such as an RF-ID tag in an identification (ID) badge. The instrument may have one or more controlled aspects. Examples of controlled aspects include: taking a reading; activating an x-ray beam, a laser beam or a spark generator; and any aspect of the instrument that may be dangerous or expensive to activate or for some other reason should be performed only by an authorized person or under controlled circumstances. Prior to activating a controlled aspect of the instrument, the instrument scans for a contactless memory within the vicinity of the instrument. If the instrument reads a contactless memory that contains information identifying an authorized person, the instrument enables the controlled aspect of the instrument. On the other hand, if the instrument does not detect an authorizing contactless memory, the instrument does not enable the controlled aspect of the instrument. Instead, the instrument may display an error message on a screen, provide some other indication or simply remain in its status quo.

The instrument may scan for an authorizing contactless memory prior to each time the instrument enables the controlled aspect of the instrument. Optionally or alternatively, the instrument may scan for the authorizing contactless memory: once upon startup; periodically; after a predetermined number of analyses; after a predetermined amount of time during which the instrument goes unused; or according to another scheme.

Automatically Setting Operating Parameters of an Analytical Instrument

In accordance with embodiments of the present invention, methods and apparatus are disclosed for automatically setting or changing operational parameters of an analytical instrument. Some hand-held analytical instruments may be used with optional stands or docking stations (collectively hereinafter referred to as "stands"). When such an instrument is mounted in a stand, the stand may provide electrical power, cooling, gas to purge air from an analytical gap within the instrument and/or other supplies, a closeable shielded cover or services to the instrument or to the operator. Under these circumstances, the instrument may be capable of operating differently than if the instrument were not connected to the stand. For example, the external power supply and cooling provided by the stand may enable the instrument to operate an x-ray source at a higher power level than if the instrument were powered and cooled solely by the instrument's internal battery. Operating differently than if the instrument were not connected to a stand is referred to herein as "operating in an enhanced mode." Under some circumstances, operating the x-ray source at a higher power may be dangerous, absent shielding to protect an operator or others. The stand may provide a closeable shielded cover, and the instrument may determine whether the cover is open or closed and enable the x-ray source only if the cover is closed.

A stand may contain a contactless memory, such as an RF-ID tag. The memory may store information that indicates the memory is associated with a stand. This indication may imply a set of one or more supplies and/or services the stand is capable of providing to an instrument docked with the stand. For example, the memory may store a model number of the stand, and each stand model may be known to provide a known set of supplies and/or services. Optionally, the memory may include information that identifies the supplies and/or services the stand is capable of providing.

An instrument may include a contactless memory reader, such as an RF-ID reader. If the instrument is mounted in a stand and the stand includes a contactless memory, the instrument reads the stand's contactless memory and automatically sets operational parameters of the instrument in accordance with supplies and/or services the stand is capable of providing. Thus, the instrument may automatically operate in an enhanced mode as a result of being mounted in the stand. Optionally, before, during or after taking each measurement, the instrument may store information in a contactless memory associated with the sample analyzed by the instrument to indicate the mode (such as enhanced or normal) in which the instrument was operating while the sample was analyzed. Optionally or alternatively, the instrument may store information in the sample's memory to indicate one or more specific parameters (such as x-ray power level or arc/spark voltage or current profile), under which the instrument operated when the sample was analyzed.

Optionally, the instrument may automatically determine one or more operating parameters (such as maximum x-ray beam power) based on information in an operator's contactless memory. For example, some operators may be authorized to operate an XRF analyzer at a higher x-ray beam power than other, less qualified, operators.

An instrument may use information from a combination of contactless memories to determine one or more operating parameters. For example, an instrument may read from a memory in a stand and from a memory in an operator's ID badge to determine one or more operating parameters. In this case, the instrument may operate in an enhanced mode, if the stand supports such a mode and the operator is authorized to operate the instrument in such a mode.

Optionally or alternatively, the instrument includes a contactless memory that stores information, such as a model number, indicating that the memory is associated with an instrument. The information may, but need not, include a list of characteristics of the instrument, such as a type of source (e.g., x-ray, laser, spark, etc.) used by the instrument to produce an excitation signal. The information may include operational parameters, such as power levels, at which the instrument is capable of operating if the instrument were to be provided with external electrical power, cooling, etc. The information may include a list of supplies and/or services that the instrument requires before operating in the enhanced mode. The information may also include a quantification of the supplies and/or services that the instrument requires to operate in the enhanced mode. For example, the information may indicate that the instrument requires 7 VDC at 4.0 amps of electrical power and 100 BTU/hour of cooling in order to operate the instrument's x-ray source at a high power level.

A stand may include a contactless memory reader, such as an RF-ID reader. If an instrument with a contactless memory that stores information about the instrument is mounted in a stand with a contactless memory reader, the stand may ascertain a set of supplies and/or services the stand is to supply to the instrument in order to enable the instrument to operate in an enhanced mode. Thus, the stand need not necessarily provide supplies and/or services that the instrument does not need.

Optionally, the stand may modify contents of a contactless memory associated with the stand to indicate to the instrument when the stand is prepared to supply the required supplies and/or services or if a problem develops within the stand that prevents the stand from providing a supply or service that the instrument requires or requested. Similarly, the instrument may modify contents of a contactless memory associated with the instrument to indicate status information to the stand, such as if additional cooling is required or the instrument is being shut down and therefore no longer needs the supplies and/or services provided by the stand. Thus, the stand and the instrument may communicate with each other by modifying contents of their respective contactless memories.

Hand-Held Analyzer with RF-ID Reader and/or Writer

RF-ID tags, in accordance with the present disclosure, can take many forms. FIG. 1 is a perspective view of an exemplary sample 100 with an RF-ID tag 102 attached thereto, according to one embodiment of the present invention. The RF-ID tag 102 may be a passive or an active RF-ID tag. The RF-ID tag 102 may be attached to the sample 100 before, during or after analysis by an instrument. As previously noted, the RF-ID tag 102 may have been attached to the sample 100 much earlier than the analysis. For example, the RF-ID tag 102 may have been attached to the sample 100 by a manufacturer of the sample 100. Optionally, the RF-ID tag 102 may include human-readable indicia, such as text, and/or computer-readable indicia, such as a barcode.

In some instances, it may be preferable to removably attach an RF-ID tag to a sample or to attach an RF-ID tag to a loop or a hole in the sample. FIG. 2 is a perspective view of a fob 200 that includes an RF-ID tag (shown in phantom at 202). The fob 200 includes a "key ring" 204 for attachment to a sample (not shown). Alternatively, a carabiner or other releasable or nonreleasable attachment mechanism may be used.

It may not be practical to attach RF-ID tags some types of samples, such as particularly small samples or samples of loose material, such as soil. FIG. 3 is a plan view of a bag 300, with an RF-ID tag 302 attached thereto, that may be used for these and other types of samples. The bag 300 may be made of plastic or another suitable material for storing the sample. The bag 300 shown in FIG. 3 includes a zipper 304, so the bag 300 may be opened and resealed multiple times. However, a one-time sealing mechanism (not shown) that, once sealed, cannot be readily opened may be used.

FIG. 4 is a perspective view of an XRF instrument 400 that includes an RF-ID writer 402, including a loop antenna 404, according to one embodiment of the present invention. A processor 403 (with an associated memory 405 for storing instructions and data for the processor 403) is coupled to the RF-ID writer 402 to control operation of the RF-ID writer 402. The RF-ID writer 402 may include an RF-ID writer or an RF-ID reader/writer housed in an integrated circuit. For example, an appropriate device is available from Texas Instruments, Dallas, Tex. under the part number TRF7960 or TRF7961.

The XRF instrument 400 may also include a touch-sensitive display screen 406 and user interface buttons 408, by which an operator may interact with the instrument 400, and a snout 410. If the snout 410 is metal, the antenna 404 may be oriented differently or may be located elsewhere in the instrument 400, such as in the handle 413 or in the rear 415 of the instrument, so the antenna 404 is not proximate the snout 410. The instrument 400 may include a rechargeable battery 411 for powering components of the instrument 400. In operation, the operator places a front portion 412 of the snout 410 against a sample. The instrument 400 may include a spring-loaded interlock switch 414, which must be fully depressed against the sample before the instrument 400 will produce an x-ray beam. The operator actuates the instrument 400 by depressing a trigger 416. The instrument 400 includes a source (not shown) of x-rays, such as an x-ray tube.

Upon actuation, the instrument 400 activates the x-ray source and emits an x-ray beam excitation signal through a window 418. The x-ray beam strikes the sample and excites a portion of the sample, thereby producing an XRF response signal from the sample. The response signal enters the instrument 400 via the window 418 and is detected by a detector (not shown) in the instrument 400. The processor (not shown) is also coupled to the detector and is programmed by instructions stored in a memory to control the x-ray source and to process an output signal from the detector.

The processor displays information, such as a chemical composition of the sample or an alloy name or identifier deduced from the chemical composition, on the screen 406. Additional information about the structure and operation of the instrument 400 is available in the above-referenced U.S. Provisional Patent Application No. 60/889,465, titled "Small Spot X-Ray Fluorescence (XRF) Analyzer," although not all aspects of the small spot XRF analyzer disclosed in the referenced provisional patent application are required in embodiments of the present invention.

Figure 5:
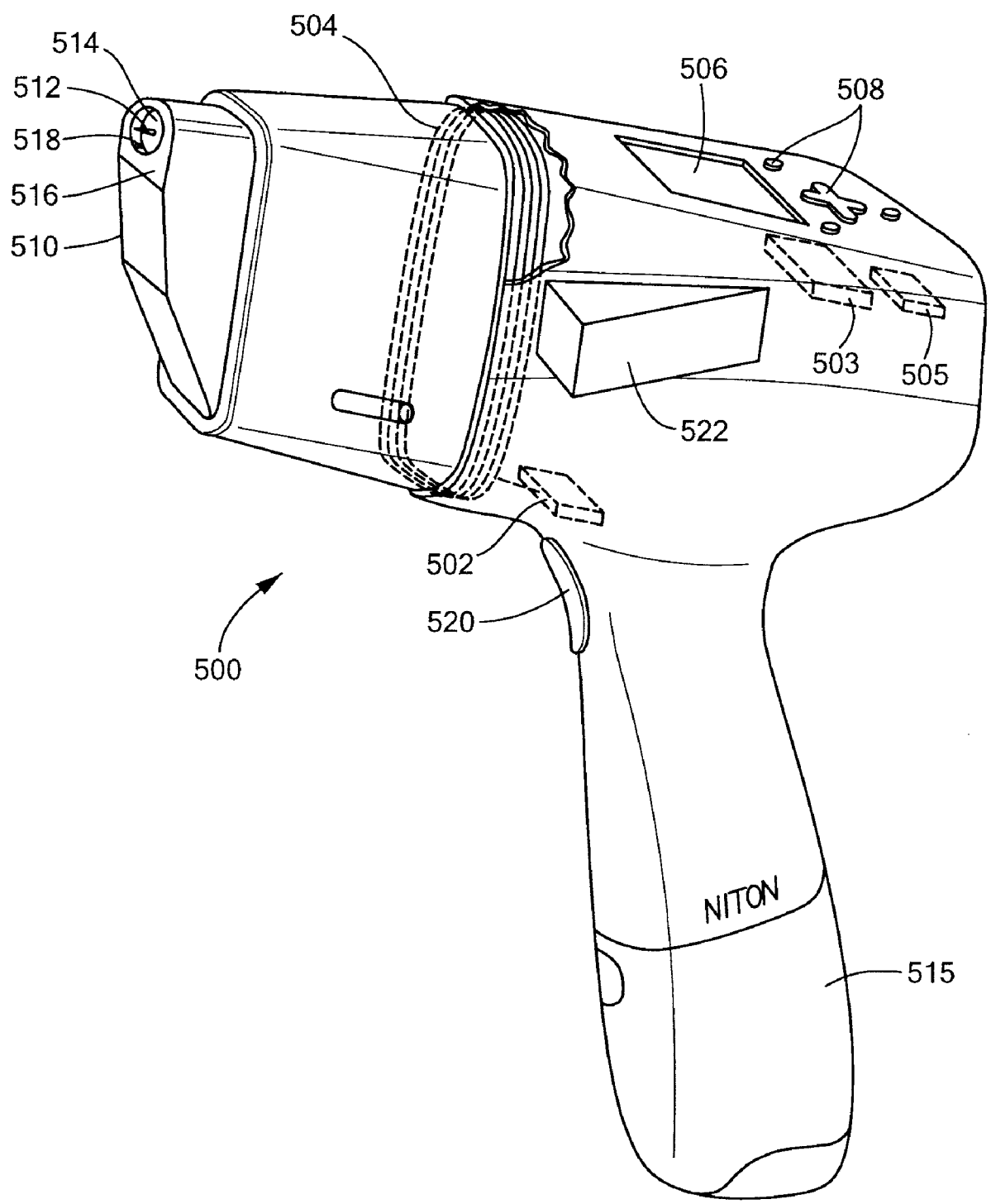
FIG. 5 is a perspective view of an optical emission spectroscopy (OES) instrument that includes an RF-ID reader, writer or reader/writer, according to one embodiment of the present invention.

FIG. 5 is a perspective view of an OES instrument 500 that includes a processor (not shown) and an associated memory (not shown) for controlling operation of the instrument 500, as with the XRF instrument 400 described above with respect to FIG. 4. The OES instrument 500 (FIG. 5) includes an RF-ID writer 502, including a loop antenna 504, according to one embodiment of the present invention. The RF-ID writer 502 may include an RF-ID writer or an RF-ID reader/writer housed in an integrated circuit. For example, an appropriate device is available from Texas Instruments, Dallas, Tex. under the part number TRF7960 or TRF7961. The processor is coupled to the RF-ID writer 502 to control operation of the RF-ID writer 502.

The OES instrument 500 also includes a touch-sensitive screen 506 and user interface buttons 508, by which an operator may interact with the instrument 500, a snout 510 and an electrode 512 within a hollow portion 514 of the snout 510. As discussed above, with respect to FIG. 4, if the snout 510 is metal, the antenna 504 may be oriented differently or may be located elsewhere in the instrument 500. The instrument 500 may include a rechargeable battery 515 for powering components of the instrument 500. In operation, the operator places a front portion 516 of the snout 510 against a sample. The instrument 500 may purge air from the hollow portion 514 by introducing a gas, such as helium, through a port 518 into the hollow portion 514. The operator actuates the instrument 500 by depressing a trigger 520. The instrument 500 includes a spark generator (not shown) coupled to the electrode 512.

Upon actuation, the instrument 500 generates an excitation signal by activating the spark generator and thereby causing an arc/spark from the electrode 512 to the sample. The arc/spark excites a portion of the sample, thereby producing an OES response signal from the sample. The response signal enters the instrument 500 via the port 518 and is directed by one or more mirrors (not shown) to a spectrometer, a portion of which is shown at 522. The spectrometer 522 acts as a detector. The spectrometer 522 is coupled to the processor (not shown), which is programmed by instructions stored in a memory to control the spark generator and to process the output signal from the spectrometer 522.

The processor displays information, such as a chemical composition of the sample or an alloy name or identifier deduced from the chemical composition, on the screen 506. Additional information about the structure and operation of the instrument 500 is available in the above-referenced U.S. Provisional Patent Application No. 60/891,408, titled "Hand-Held, Self-Contained Optical Emission Spectroscopy (OES) Analyzer," although not all aspects of the OES analyzer disclosed in the referenced provisional patent application are required in embodiments of the present invention.

Although an XRF instrument 400 and an OES instrument 500 have been described, embodiments of the present invention may include or be used with other types of analyzers, such as laser-induced breakdown spectroscopy (LIBS), glow discharge (GD) analyzers, Raman spectrometers, mass spectrometers, etc. The descriptions of uses with XRF or OES instruments 400 or 500 are, therefore, merely exemplary and not limiting.

As noted, storing information related to an analyzed sample (such as a chemical composition of the sample or information about the sample's origin), an instrument used to analyze the sample or an operator of the instrument can be very useful. The RF-ID writer 402 or 502 of the XRF instrument 400 of FIG. 4 or the OES instrument 500 of FIG. 5 or a similar RF-ID writer in another portable or non-portable instrument may be used to store this type of information in a contactless memory, such as the RF-ID tags 102, 202 or 302 shown in FIGS. 1-3. The RF-ID tags 102, 202 or 302 may be written before, during or after the analysis by the instrument. One of the RF-ID tags 102, 202 or 302 may be written by bringing a portion of the instrument 400 or 500 that contains the loop antenna 404 or 504 proximate the RF-ID tag and operating the RF-ID writer 402 or 502.

The RF-ID tag writer 402 or 502 may scan for RF-ID tags and, therefore, automatically detect the presence of an RF-ID tag within range and, thereafter, automatically write the analytical information, etc. to the RF-ID tag. Alternatively or optionally, an operator may use the user interface buttons 408 or 508 or the touch-sensitive screen 406 or 506 to command the RF-ID writer 402 or 502 to scan for or write the RF-ID tag.

If the RF-ID tag 102, 202 or 302 already contains, or may already contain, information that should be preserved, the instrument 400 or 500 may include an RF-ID reader/writer (or an RF-ID reader and a separate RF-ID writer) in place of the RF-ID writer 402 or 502. (In other respects, FIGS. 4 and 5 may be used to describe instruments with RF-ID reader/writers or both readers and separate writers, and reference numerals 402 and 502 will be used to also represent such RF-ID readers and/or writers.) An instrument 400 or 500 may interrogate the RF-ID tag 102, 202 or 302 to read data stored therein. Then, when the instrument 400 or 500 writes new analytical information to the memory, the RF-ID writer or reader/writer 402 or 502 may write to a location in the memory so as to avoid overwriting the previously stored information. Alternatively or optionally, the writer or reader/writer 402 or 502 may re-write the previously stored information in the same location in the memory as the information was previously stored or in a different location.

Figure 6:
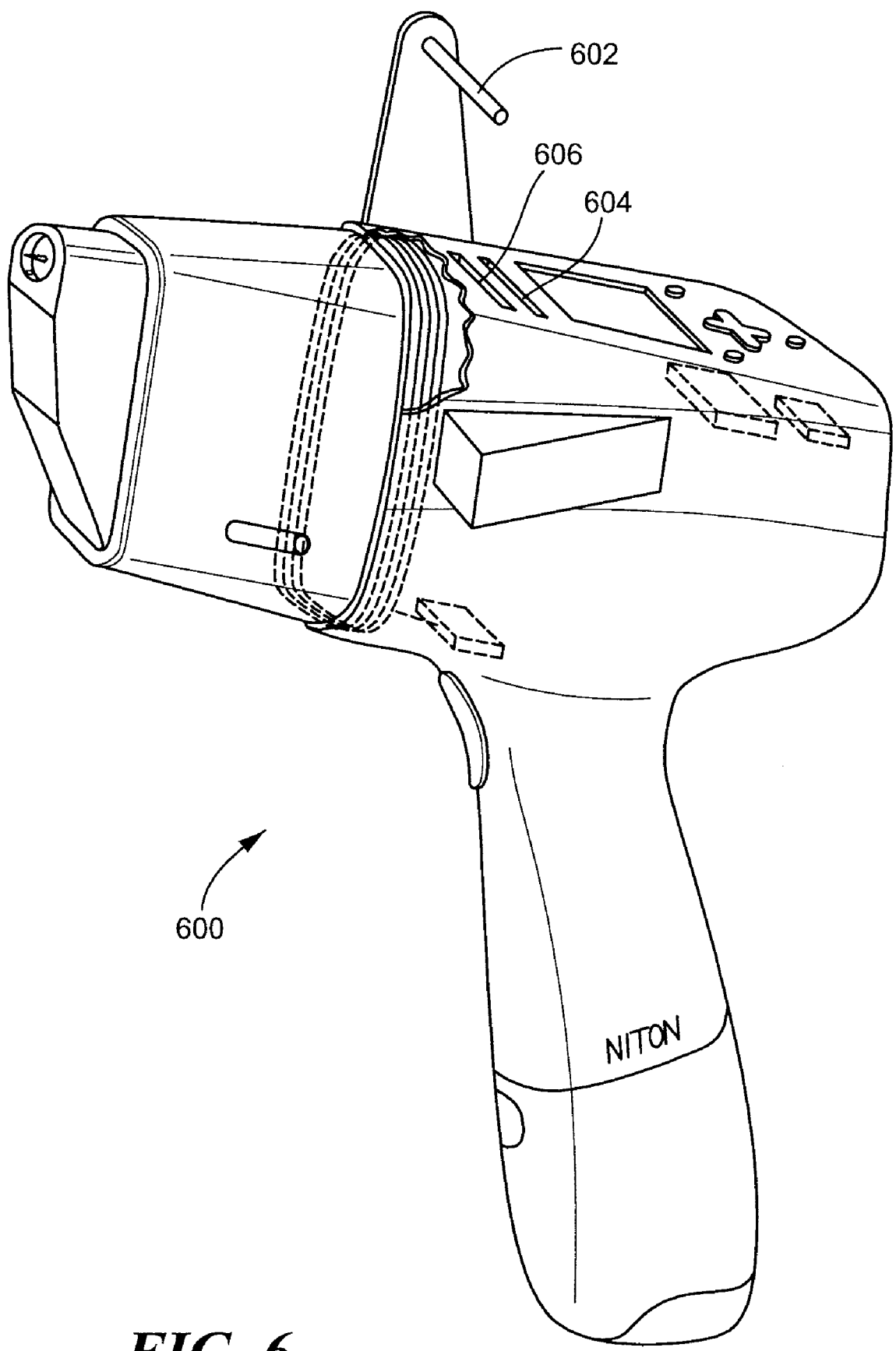
FIG. 6 is a perspective view of an analytical instrument that includes an RF-ID tag dispenser spindle, according to one embodiment of the present invention.

In some instances, a user may have a supply of loose RF-ID tags that may be attached to samples before or after the RF-ID tags are written to. In other instances, the samples already have RF-ID tags, such as those attached by manufacturers. In yet other instances, it may be convenient for the instrument 400 or 500 to dispense RF-ID tags. FIG. 6 is a perspective view of an instrument 600 that includes a dispenser spindle 602, on which a spool (not shown) of RF-ID tags may be mounted. (Although an OES instrument 600 is shown in FIG. 6, an RF-ID tag dispenser, as described herein, may be included in an XRF or other type of instrument.) The instrument 600 includes a feed slot 604 and a dispensing slot 606 in the housing of the instrument 600.

Figure 7:
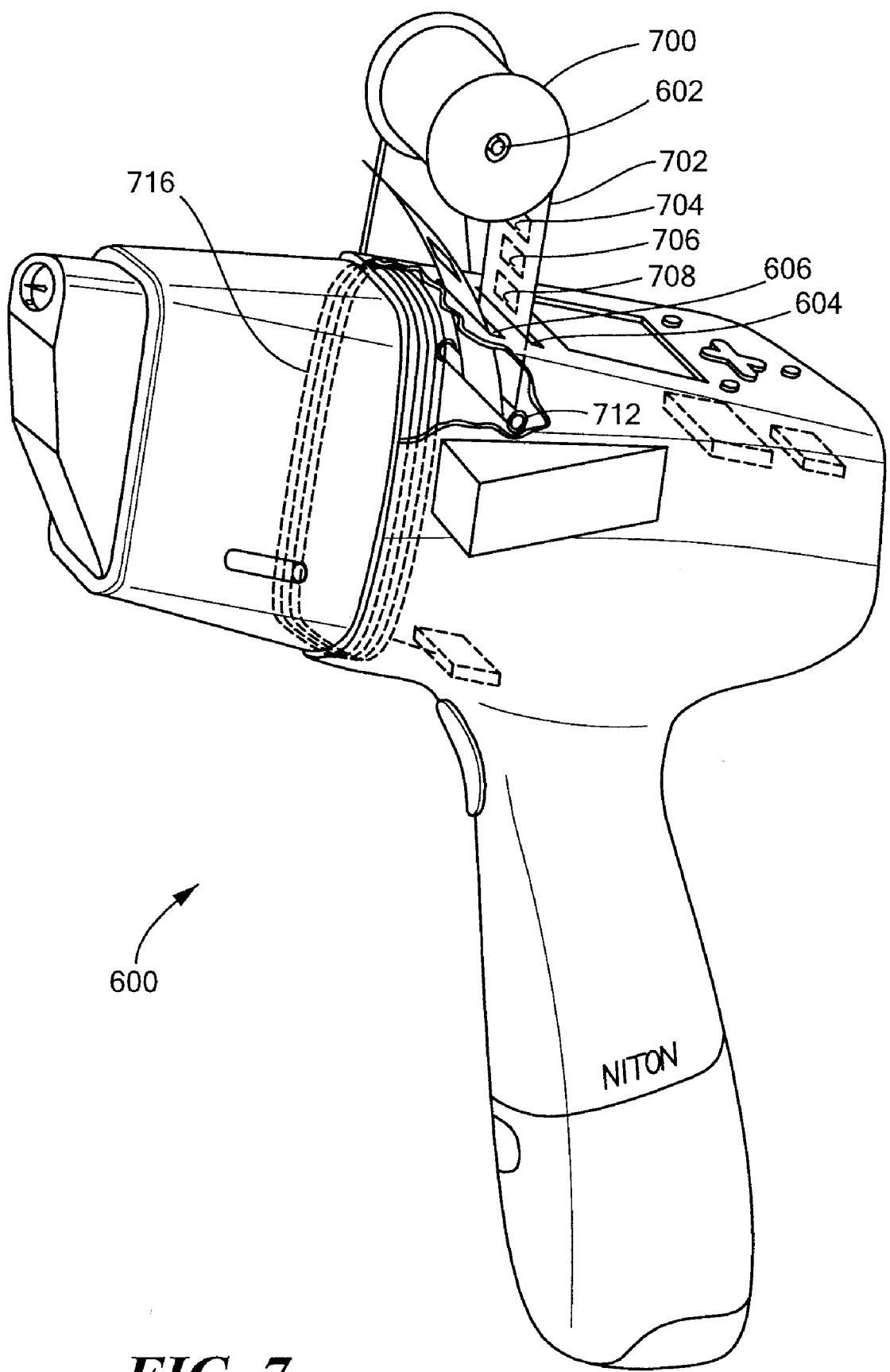
FIG. 7 is a perspective view of the instrument of FIG. 6 with a spool of RF-ID tags mounted thereon, according to one embodiment of the present invention.

As shown in FIG. 7, a spool 700 of RF-ID tags may be mounted on the spindle 602. The spindle 700 contains a roll of backing tape 702, on which a series of RF-ID tags 704, 706, 708, etc. is attached. The backing tape 702 is fed into the feed slot 604. The backing tape 702 loops around a second spindle 712 and then exits the housing via the dispensing slot 606. A pinch roller (not shown) and drive motor (not shown) operate under control of the processor to advance the backing tape 702 as needed.

The loop of backing tape 702 around the second spindle 712 brings the backing tape 702 and, therefore, each individual RF-ID tag attached to the backing tape 702 proximate the loop antenna 716 to facilitate writing one RF-ID tag at a time. The RF-ID tags may be spaced along the backing tape 702 such that only one of the RF-ID tags on the backing tape 702 is within range of the loop antenna 716 at one time. Optionally, RF shielding (not shown) may be used to prevent other RF-ID tags on the backing tape 702 from receiving sufficient radiation from the loop antenna 716 to activate the RF-ID tags.

Once an RF-ID tag has been written to by the instrument 600 and the RF-ID tag exits the instrument 600 via the dispensing slot 606, the RF-ID tag may be removed from the backing tape 702 and attached to the sample. Optionally, before dispensing the RF-ID tag, the instrument may attempt to read the RF-ID tag to ensure it is readable and the information was correctly stored in the memory.

Each RF-ID tag may have an adhesive backing to facilitate attaching the RF-ID tag to the sample. Optionally or alternatively, a user may apply an adhesive to each RF-ID tag to attach the RF-ID tag to the sample, or the user may attach the RF-ID tag to the sample by covering the RF-ID tag with an adhesive tape or by any other suitable mechanism.

Alternatively or optionally, as shown in FIG. 4, an instrument 400 may include a depression 420 in the instrument's housing, into which an individual RF-ID tag 422 may be placed (as indicated by an arrow 424) while the RF-ID writer 402 interrogates and/or writes to the RF-ID tag. Alternatively or optionally, the instrument housing may have indicia to indicate where the RF-ID tag 422 should be held while the RF-ID tag is written. As discussed above, the RF-ID tag 422 may have an adhesive backing to facilitate attaching the RF-ID tag to a sample.

Figure 8:
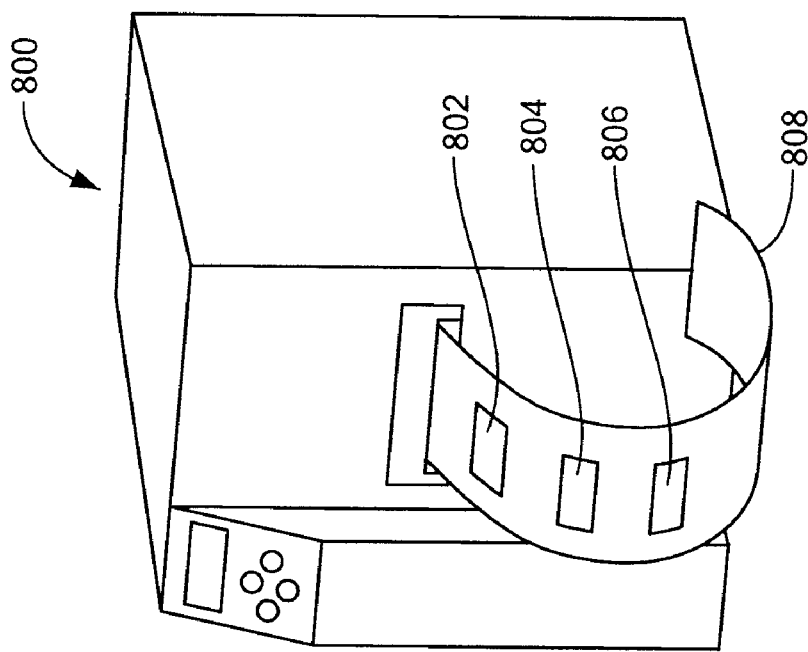
FIG. 8 is a perspective view of an alternative RF-ID tag encoder-dispenser, according to one embodiment of the present invention.

FIG. 8 is a perspective view of an alternative RF-ID tag encoder-dispenser 800, according to one embodiment of the present invention. The RF-ID tag encoder-dispenser 800 is a stand-alone unit. A hand-held instrument 400 or 500 or a non-portable instrument (not shown) may send information and commands to the tag encoder-dispenser 800 to cause the tag encoder-dispenser 800 to encode an RF-ID tag and dispense the tag. The instrument may communicate with the encoder-dispenser 800 via a wireless link, such as an infrared or a Bluetooth link, or any other suitable wired or wireless link. The RF-ID tag encoder-dispenser 800 is shown dispensing RF-ID tags 802, 804 and 806 on a backing tape 808. A suitable RF-ID tag encoder-dispenser is available from Weber Marking Systems, Inc., Arlington Heights, Ill., under the designation R4Mplus, R110XiIIIPlus or R170XiIIIPlus.

Figure 9:
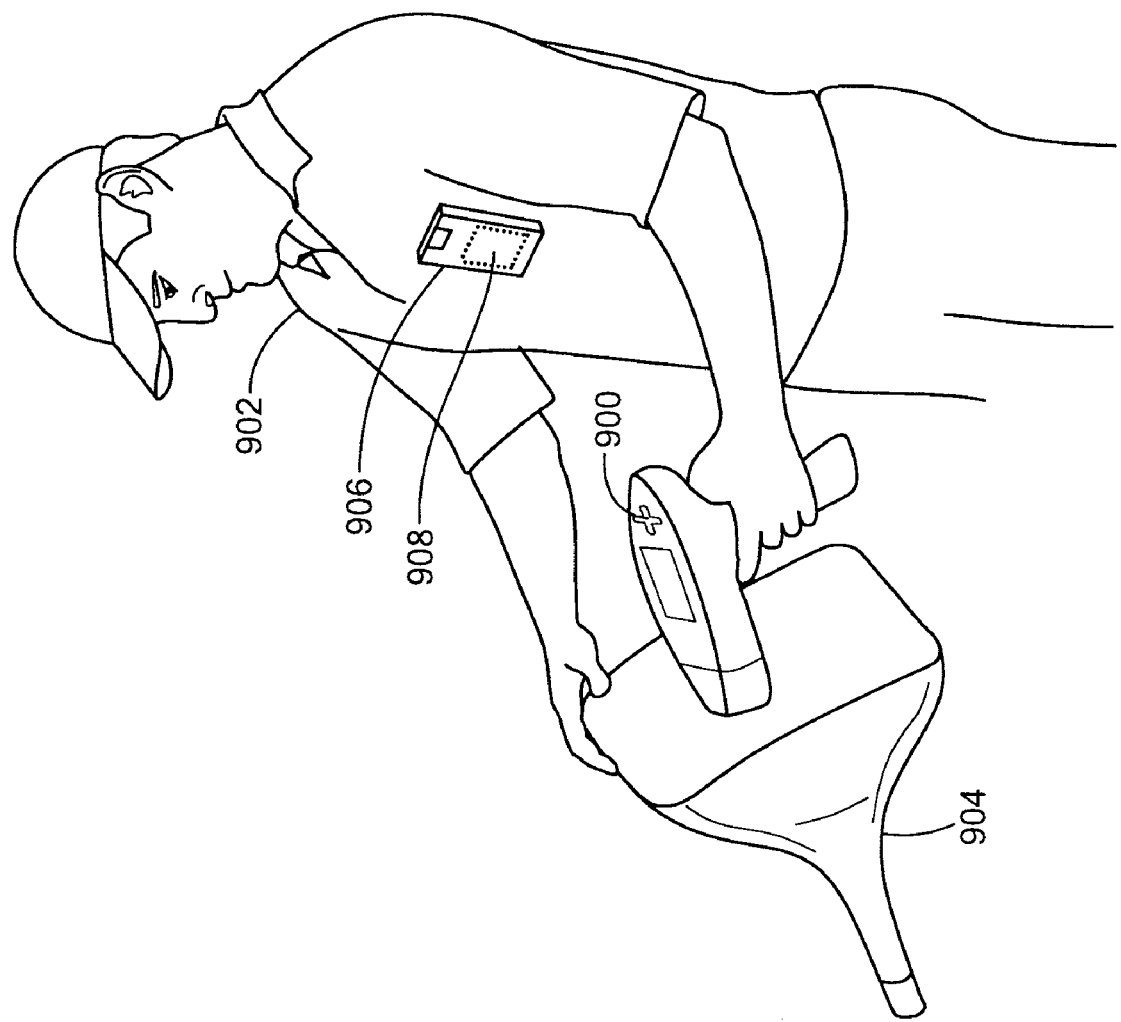
FIG. 9 is a perspective view of an exemplary context in which an instrument may prevent unauthorized use, or control one or more aspects of its operation, in accordance with embodiments of the present invention.

FIG. 9 is a perspective view of an exemplary context in which an instrument 900 may prevent unauthorized use, or control one or more aspects of its operation, in accordance with embodiments of the present invention. The instrument 900 is shown being used by an operator 902 to test a sample 904. The operator 902 wears an identification (ID) badge 906, which includes an RF-ID tag (shown in phantom at 908). The instrument 900 includes an RF-ID reader (not shown, but similar to the RF-ID tag reader 402 or 502, including loop antenna 404 or 504, shown in FIG. 4 or 5). A suitable RF-ID reader is available from SkyeTek, Inc., Westminster, Colo., under the designation SkyeModule M1-mini.

As noted, the instrument 900 may have one or more controlled aspects. Prior to activating a controlled aspect of the instrument, or prior to operating an aspect of the instrument in a predetermined mode, the instrument scans for a contactless memory, such as the RF-ID tag 908 in the operator's ID badge 906, within range of the instrument. If the instrument reads a contactless memory that contains information identifying an authorized person, the instrument enables the controlled aspect of the instrument or operates the aspect of the instrument in the predetermined mode. Thus, for example, the instrument 900 may enable a spark generator only if an authorized operator is using the instrument, or the instrument may determine a maximum x-ray beam power, based on information in the operator's RF-ID tag 908.

Figure 10:
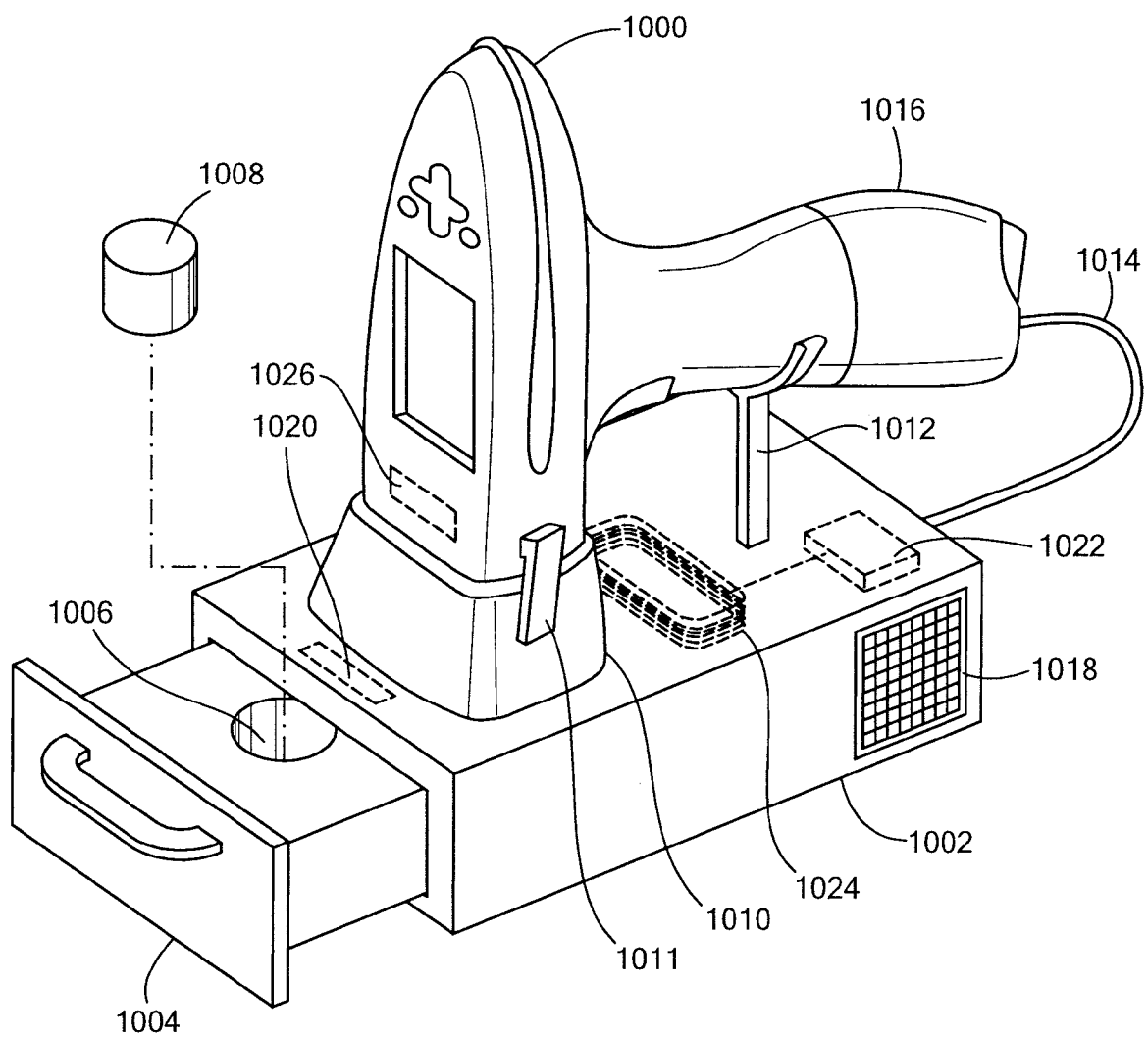
FIG. 10 is a perspective view of an instrument and a docking station ("stand"), to which the instrument may be docked, according to embodiments of the present invention.

FIG. 10 is a perspective view of an instrument 1000 attached ("docked" or, equivalently, "mounted") to a stand 1002. The stand 1002 may include a drawer 1004 with a depression or a bore 1006, into which a sample 1008 may be inserted. When the drawer 1004 is closed, a sample within the depression or bore 1006 is positioned adjacent the instrument 1000 for analysis thereby. The stand 1002 includes a receiver 1010, into which a portion of the instrument 1000 is inserted. The receiver 1010 may include one or more latches (one visible at 1011) to secure the instrument 1000 to the stand 1002. The instrument 1000 may include one or more grooves, notches, holes, bosses, studs or other features that cooperate with the latches to secure the instrument 1000 to the stand 1002. Optionally or alternatively, the instrument 1000 may be held in the receiver 1010 by another type of releasable mechanism, such as a spring-loaded projection that mates with a detent, magnets, friction or merely by gravity. An optional bracket 1012 supports a portion of the weight of the instrument 1000 and stabilizes the instrument 1000.

As noted, the stand 1002 may provide one or more supplies or services to the instrument 1000. Some or all of these supplies or services may be provided via electrical, fluid, mechanical, heat transfer or other suitable connectors on the stand 1002 and corresponding connectors on the instrument 1000 that mate with each other when the instrument 1000 is docked in the stand 1002. These connectors may be located in any suitable location on the instrument 1000 and on the stand 1002. For example, some or all of these connectors may be located on the snout 410 (FIG. 4) or 510 (FIG. 5) of the instrument 1000. Such snout-located connectors may mate with corresponding connectors located within the receiver 1010. Optionally or alternatively, supplies or services, such as cooling, may be provided via physical contact or proximity between the instrument 1000 and the stand 1002.

Optionally or alternatively, the stand 1002 may be connected to the instrument 1000 via a cable 1014 extending to a "dummy" battery 1016, which attaches to the instrument 1000 in the same way the rechargeable battery 411 or 515 (FIG. 4 or 5) attaches to the instrument 1000. The cable 1014 may include electrical connections, such as a power supply or a thermoelectric (TE) cooling circuit. The cable 1014 may also include fluid communication channels, such as for a cooling fluid or a purge gas.

In one embodiment, an inside surface (not visible) of the receiver 1010 is cooled by the stand 1002, so the docked instrument 1000 may operate at a higher power level and/or for a longer time than if the instrument 1000 were being operated separate from the stand 1002. The snout 410 or 510 may contact the cooled surface of the receiver 1010 to conduct heat from the instrument 1000.

The receiver surface may be cooled by forced air provided by a fan (not visible), by another circulating fluid that flows through a refrigeration unit (not visible) or a heat sink (not shown), by TE cooling or by any other suitable mechanism. The stand 1002 may introduce forced cooling air into the instrument 1000 to cool components therein. If the instrument 1000 utilizes TE cooling, such as to cool an optical sensor, the stand 1002 may include a hot side of the TE heat exchanger, and the cold side of the TE heat exchanger in the instrument 1000 may be electrically connected to the hot side of the heat exchanger. The stand 1002 may include an air intake and/or exhaust port 1018 that is used in conjunction with the stand's cooling mechanism.

As noted, the instrument 1000 may automatically set or change operational parameters as a result of being docked in the stand 1002. The stand 1002 may include an RF-ID tag 1020, which the instrument 1000 may interrogate using the RF-ID reader 402 or 502 (FIG. 4 or 5). Thus, for example, by reading the RF-ID tag 1020 in the stand 1002, the instrument 1000 may ascertain the supplies and/or services the stand 1002 is capable of providing.

Also as noted, the instrument 1000 may include an RF-ID tag 1026, which the stand 1002 may interrogate using an RF-ID reader 1022, including a loop antenna 1024. Thus, for example, by reading the RF-ID tag 1026 in the instrument 1000, the stand 1002 may ascertain operational parameters of the instrument 1000 or services or supplies that the instrument 1000 may require.

Figure 12:
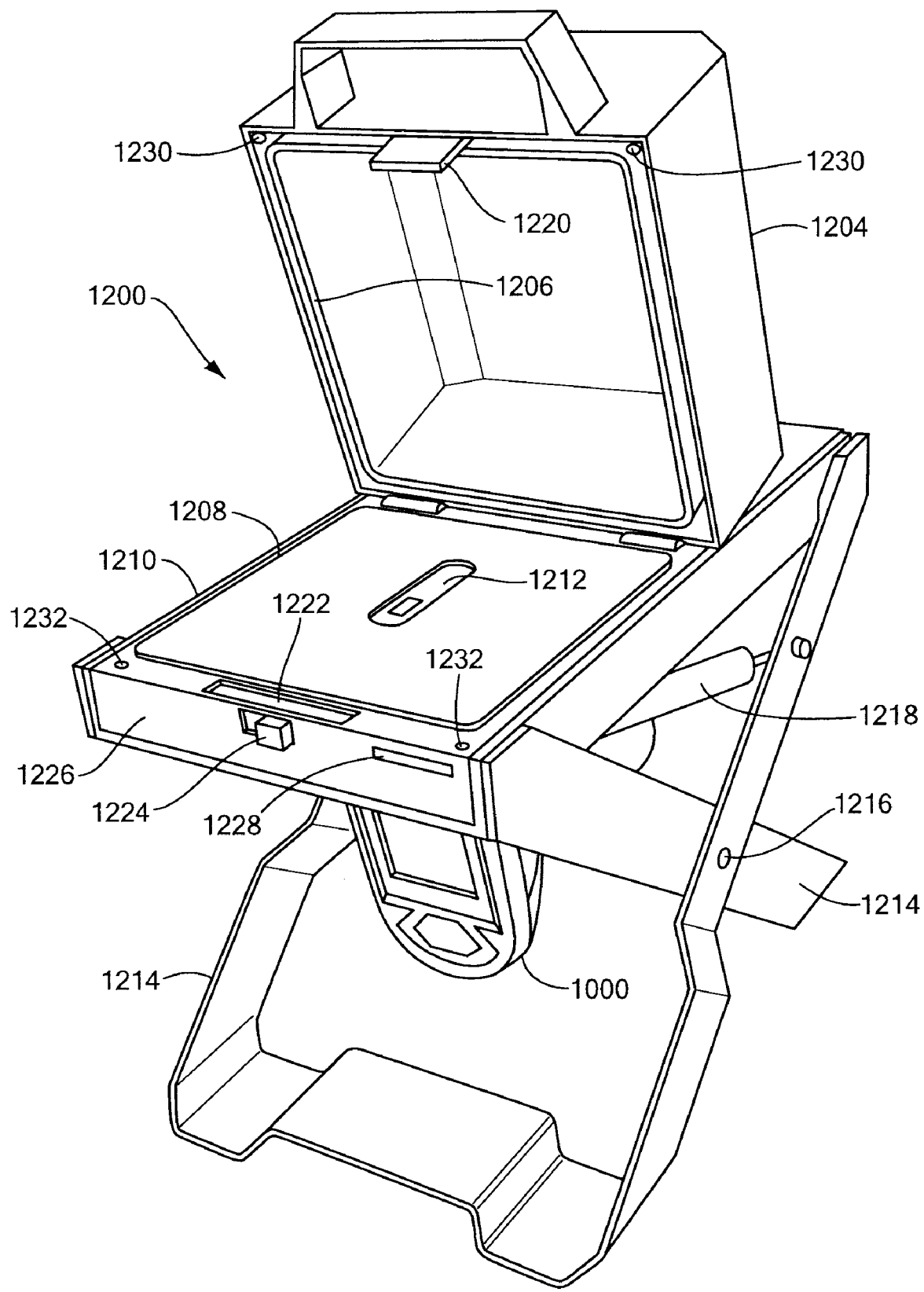
FIG. 12 is a perspective view of another stand and an instrument docked to the stand.
Figure 14:
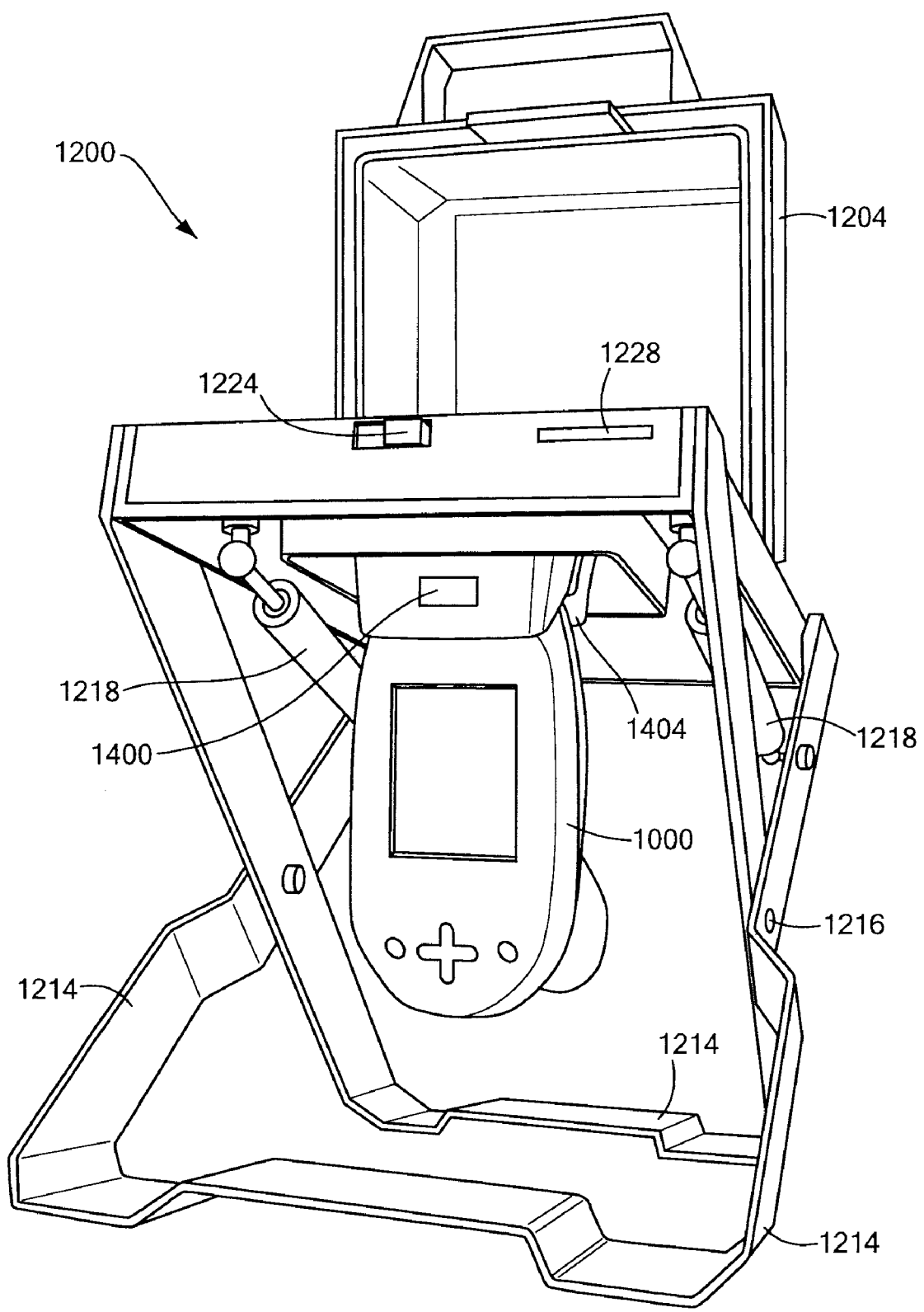
FIG. 14 another perspective view of the stand of FIG. 12 from a lower viewpoint than that provided in FIGS. 12 and 13.

In some cases, an operator or others should be protected from x-rays, laser beams, sparks or other hazards produced by an analytical instrument or by a by-product of, or possible effect (such as an explosion) from, an analysis performed by the instrument. FIG. 12 is a perspective view of another stand 1200, on which an analytical instrument 1000 is detachably docked. The stand 1200 includes a hinged, recloseable cover 1204, which is suitably shielded to protect an operator or others. The analytical instrument 1000 is docket to the stand 1200 from below, as best shown in FIG. 14. The analytical instrument 1000 docks in a receiver 1402 and is secured to the stand 1200 by a releasable latch (one of which is visible at 1404) or another suitable mechanism, examples of which were discussed above, with respect to FIG. 10.

Returning to FIG. 12, the cover 1204 shielding may include a lead or other suitable material liner 1206, or the cover 1204 may be made of a suitably shielding material. Similarly, the stand 1200 includes a lead or other suitable material table 1208, or the base 1210 of the stand 1200 is made of a suitable shielding material. When the cover 1204 is open, the operator may place a sample on the table 1208 (or directly on the base 1210, if no separate table 1208 is provided) for analysis by the analytical instrument 1000. The table 1208 and the base 1210 include openings 1212, through which the analytical instrument 1000 has access to the sample.

Figure 13:
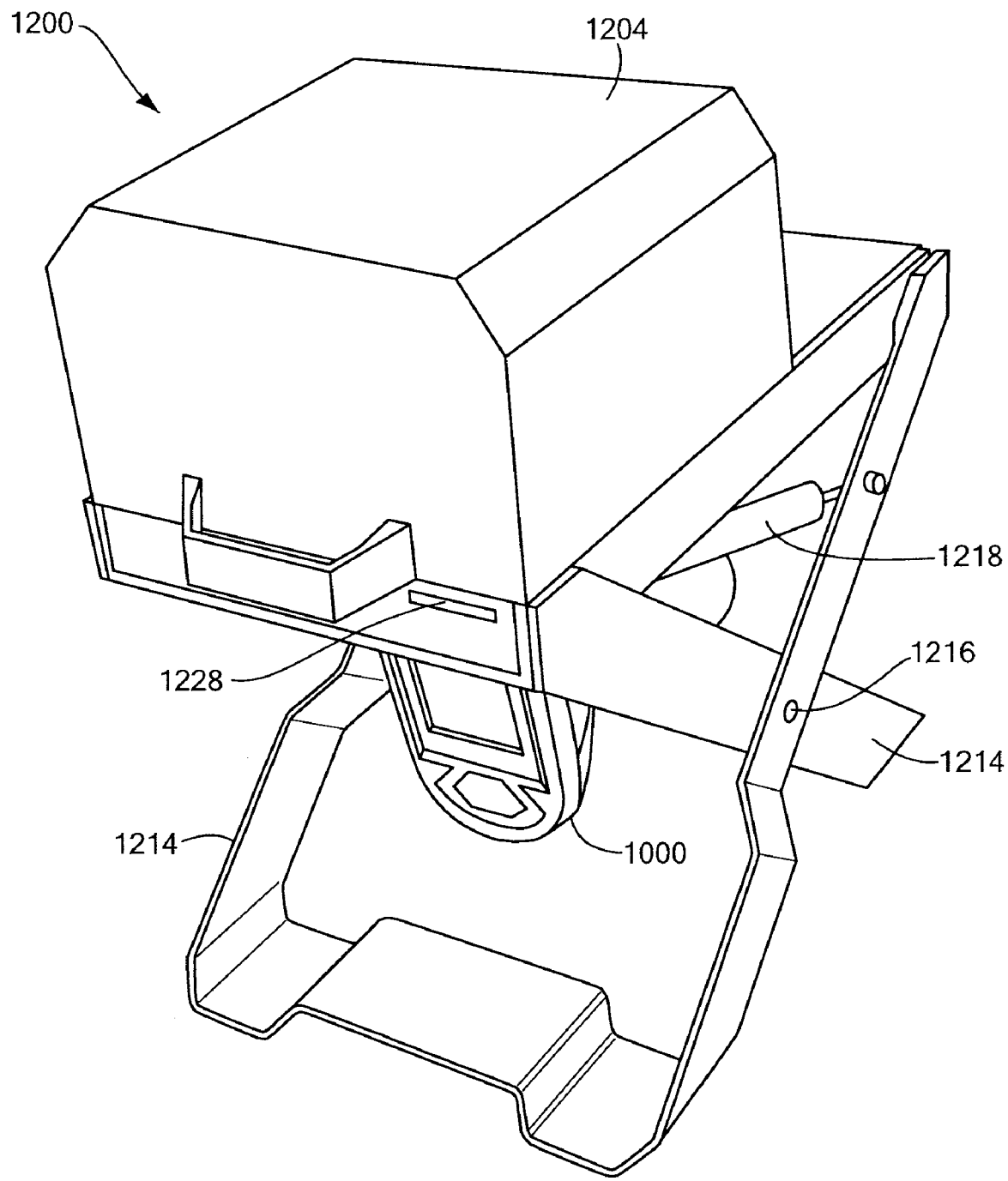
FIG. 13 is a perspective view of the stand of FIG. 12 with its cover closed.

When the cover 1204 is closed, as shown in FIG. 13, the cover liner 1206 and the table 1208 and/or the cover 1204 and the base 1210 shield the operator and others from hazards associated with analyzing the sample by the analytical instrument 1000.

For convenience, the stand 1200 may include foldable legs 1214. The legs 1214 may be folded by pivoting the legs 1214 about hinged points 1216 to make the stand more compact for storage or transport. A gas-filled shock absorber 1218 maintains the legs 1214 in either a folded or extended position.

The stand 1200 may include a latch 1220 that mates with a catch 1222. The latch 1220 may be locked or unlocked by a manual switch 1224 on a front panel 1226 of the stand 1200. The front panel 1226 may also include indicator lights, switches and other controls 1228, some or all of which may be electrically coupled to the analytical instrument 1200. The analytical instrument 1200 may be electrically and otherwise coupled to the stand 1200, as described above.

In one embodiment, the stand 1200 includes an RF-ID tag 1400 (FIG. 14). The analytical instrument 1000 reads the RF-ID tag 1400 to ascertain that the analytical instrument 1000 is docked with a stand having a cover 1204 that may be opened. The cover 1204 includes magnets 1230 (FIG. 12), and the base 1210 includes Hall-effect sensors 1232, positioned such that, when the cover 1204 is closed, the magnets 1230 are proximate the Hall-effect sensors 1232. The Hall-effect sensors 1230 are coupled to the analytical instrument 1000, so the instrument 1000 can determine whether the cover 1204 is open or closed. Optionally or alternatively, electrical contacts, miniature switches, pressure sensors or other sensors may be used to determine whether the cover 1204 is open or closed. The analytical instrument 1200 may be electrically and otherwise coupled to the Hall-effect sensors 1232, as described above.

When the analytical instrument 1000 determines that it is docked to the stand 1200 (by reading the RF-ID tag 1400), and that the cover 1204 is closed, the instrument 1000 enables operation of its x-ray tube, spark generator, laser or other source of penetrating radiation at a power level that may not be suitable, absent the shielding provided by the cover 1204 and other parts of the stand 1200. Thus, the magnets 1230, the Hall-effect sensors 1232 and the processor in the analytical instrument 1000 form an interlock to prevent unsafe operation of the analytical instrument 1000. When the analytical instrument 1000 does not detect the RF-ID tag 1400, i.e., when the instrument 1000 is not docked in the stand 1200, the processor in the analytical instrument 1000 enables operation of the x-ray tube, spark generator, laser, etc. in a different mode, i.e., at a lower power level than when the instrument 1000 is docked with the stand 1200 and the cover 1204 is closed.

Figure 11:
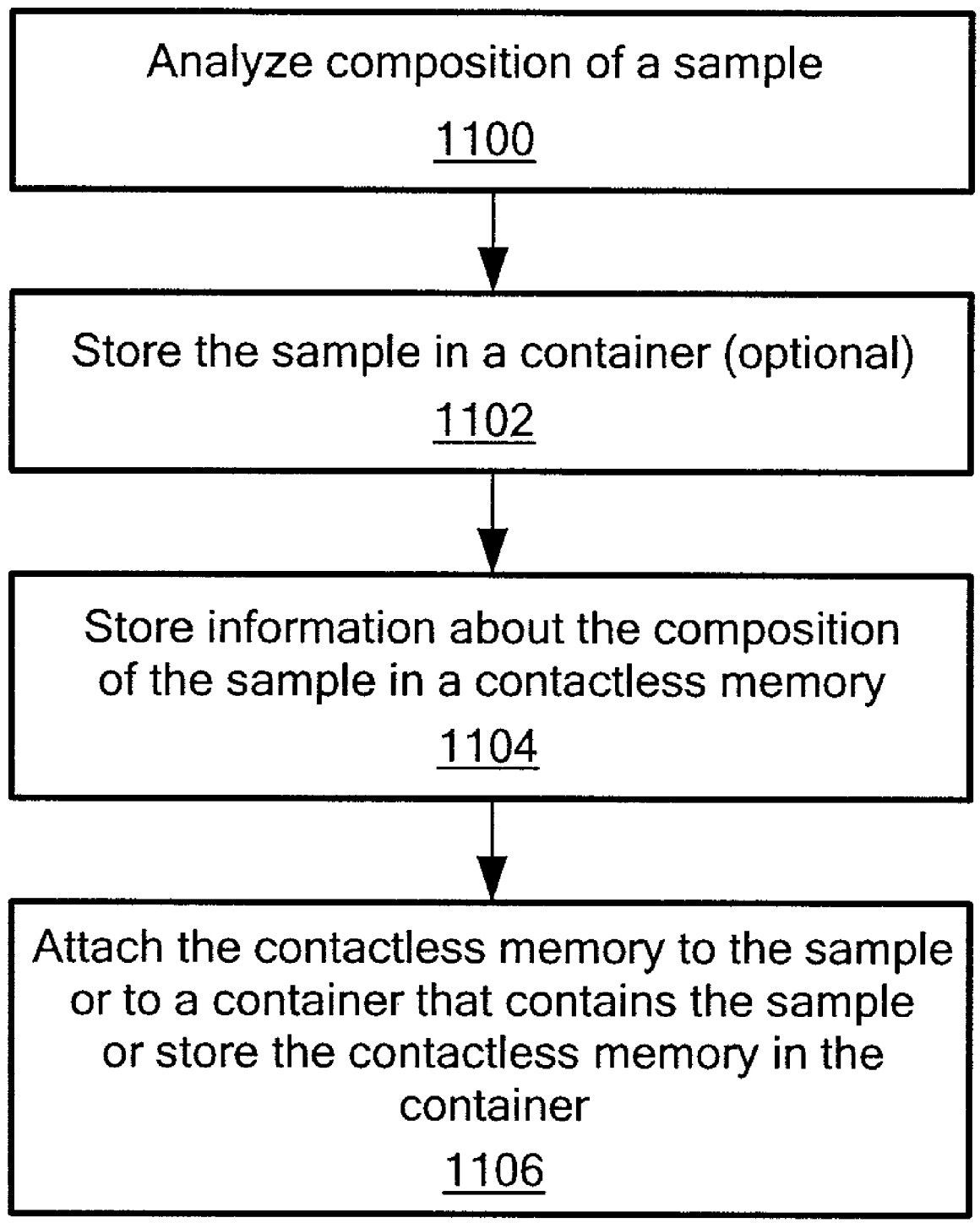
FIG. 11 is a flowchart illustrating operations performed to store information related to an analyzed sample, according to one embodiment of the present invention.

FIG. 11 is a flowchart illustrating operations performed to store information related to an analyzed sample. At 1100, composition of the sample is analyzed. At 1102, the sample is optionally stored in a container. At 1104, information about the composition of the sample is stored in a contactless memory. At 1106, the contactless memory is attached to the sample or to the container, or the contactless memory is stored in the container along with the sample.

Some embodiments of the present invention have been described as including various types of contactless memories and/or contactless memory readers, writers or reader/writers. Some of these embodiments have been described with reference to RF-ID tags and RF-ID readers, writers or reader/writers; however, other types of contactless memories may be used. In some such embodiments, barcodes may be used. After an instrument analyzes a sample, information about the sample may be suitably encoded as binary or other types of data and the encoded data may be printed as a barcode. The instrument may include a barcode printer or the instrument may communicate, such as via a wired or wireless link, to a barcode printer. The barcode may include an adhesive backing to facilitate attaching the barcode to the sample. In another embodiment, the instrument or an external writer may write the barcode directly on a surface of the sample, such as by etching the surface with a laser beam.

In other embodiments, rewritable barcodes may be used. In one such embodiment, a rewriteable card is written by a suitable writer. Such a writer is available from Datacard Group, Minnetonka, Minn., under the designation Datacard SP25 Card Printer. Additional information about rewriteable barcode is available in U.S. Pat. No. 5,521,371, titled "Rewriteable Bar Code Display Medium, and Image Display Method and Image Display Apparatus Using the Same," the contents of which are hereby incorporated by reference herein.

Barcodes may be read by hand-held barcode readers or fixed barcode readers coupled to automatic sorting equipment.

An analytical instrument has been described as including a processor controlled by instructions stored in a memory. The memory may be random access memory (RAM), read-only memory (ROM), flash memory or any other memory, or combination thereof, suitable for storing control software or other instructions and data. Some of the functions performed by the analytical instrument have been described with reference to flowcharts. Those skilled in the art should readily appreciate that functions, operations, decisions, etc. of all or a portion of each block, or a combination of blocks, of the flowcharts may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as limited.

What is claimed is:

1. A method for automatically setting an operating parameter of an analytical instrument, comprising:
   automatically determining if the analytical instrument is mounted on a stand;
   if the analytical instrument is determined to be mounted on the stand, operating the analytical instrument according to a first operating parameter; and
   if the analytical instrument is determined not to be mounted on the stand, operating the analytical instrument according to a second operating parameter different than the first operating parameter.

2. A method according to claim 1, wherein determining if the analytical instrument is mounted on the stand comprises determining if the analytical instrument is mounted on a stand that is capable of cooling at least a portion of the analytical instrument.

3. A method according to claim 1, wherein determining if the analytical instrument is mounted on the stand comprises determining if the analytical instrument is mounted on a stand that is capable of providing electrical power to the analytical instrument.

4. A method according to claim 1, wherein, according to the first operating parameter, the analytical instrument is operated at a higher power rating than according to the second operating parameter.

5. A method according to claim 1, wherein determining if the analytical instrument is mounted on the stand comprises scanning for a contactless memory associated with the stand.

6. A method according to claim 5, wherein the scanning for the contactless memory comprises scanning for a radio-frequency identification (RF-ID) tag.

7. A method according to claim 5, wherein the scanning for the contactless memory comprises scanning a barcode.

8. A method according to claim 5, wherein the scanning for the contactless memory comprises reading a magnetic stripe.

9. A method for automatically preventing unsafe operation of an analytical instrument that can operate in at least two different modes, the method comprising:
   automatically determining if the analytical instrument is mounted on a stand;
   if the analytical instrument is determined to be mounted on the stand, operating the analytical instrument according to a first of the at least two different modes only if a safety device on the stand has been activated; and
   if the analytical instrument is determined not to be mounted on the stand, operating the analytical instrument according to a second of the at least two different modes.

10. A method according to claim 9, wherein:
operating the analytical instrument according to the first mode comprises operating a source for producing a beam of penetrating radiation at a first power level; and
operating the analytical instrument according to the second mode comprises operating the source for producing a beam of penetrating radiation at a second power level less than the first power level.

11. A method according to claim 10, wherein the source for producing a beam of penetrating radiation comprises an x-ray tube.

12. A method according to claim 10, wherein the source for producing a beam of penetrating radiation comprises a laser.

13. A method according to claim 10, wherein the source for producing a beam of penetrating radiation comprises a spark source.

14. A method according to claim 9, wherein the safety device comprises a closeable cover.

15. A method according to claim 9, wherein determining if the analytical instrument is mounted on the stand comprises scanning for a contactless memory associated with the stand.

16. A method according to claim 15, wherein the scanning for the contactless memory comprises scanning for a radio-frequency identification (RF-ID) tag.

17. A method according to claim 15, wherein the scanning for the contactless memory comprises scanning a barcode.

18. A method according to claim 15, wherein the scanning for the contactless memory comprises reading a magnetic stripe.

* * * * *